US010473606B2

(12) United States Patent
Buckberry

(10) Patent No.: US 10,473,606 B2
(45) Date of Patent: Nov. 12, 2019

(54) LIQUID CONDUCTIVITY MEASUREMENT CELL

(71) Applicant: QUANTA FLUID SOLUTIONS, Alcester, Warwickshire (GB)

(72) Inventor: Clive Henry Buckberry, Warwick (GB)

(73) Assignee: Quanta Dialysis Technologies Limited, Warwickshire (GB)

( * ) Notice: Subject to any disclaimer, the term of this patent is extended or adjusted under 35 U.S.C. 154(b) by 597 days.

(21) Appl. No.: 14/785,174

(22) PCT Filed: Mar. 27, 2014

(86) PCT No.: PCT/GB2014/050976
§ 371 (c)(1),
(2) Date: Oct. 16, 2015

(87) PCT Pub. No.: WO2014/191715
PCT Pub. Date: Dec. 4, 2014

(65) Prior Publication Data
US 2016/0084785 A1    Mar. 24, 2016

(30) Foreign Application Priority Data
May 29, 2013  (GB) .................... 1309561.7

(51) Int. Cl.
| G01N 27/08 | (2006.01) |
| B29C 65/00 | (2006.01) |
| B29K 633/04 | (2006.01) |
| B29L 31/00 | (2006.01) |

(52) U.S. Cl.
CPC ......... *G01N 27/08* (2013.01); *B29C 66/0222* (2013.01); *B29C 66/304* (2013.01);
(Continued)

(58) Field of Classification Search
CPC ...................................................... G01N 27/08
See application file for complete search history.

(56) References Cited

U.S. PATENT DOCUMENTS

| 5,012,197 A | 4/1991 | Seiffert et al. |
| 2008/0285011 A1* | 11/2008 | Shakespeare .......... G01N 21/33 356/51 |

(Continued)

FOREIGN PATENT DOCUMENTS

| CN | 1 344 929 A | 4/2002 |
| DE | 27 48 809 A1 | 5/1979 |

(Continued)

OTHER PUBLICATIONS

Sep. 1, 2014 ISR for PCT/GB2014/050976.
(Continued)

*Primary Examiner* — Patrick Assouad
*Assistant Examiner* — Feba Pothen
(74) *Attorney, Agent, or Firm* — Hahn Loeser & Parks, LLP

(57) ABSTRACT

The present invention provides a liquid conductivity measurement cell comprising a chamber having an inlet, an outlet and four sensing pins of substantially equal length, said sensing pins being arranged within the chamber around an orbit, each sensing pin defining an electrode, each of said electrodes being switchable between two or more configurations of two sensing pins.

33 Claims, 4 Drawing Sheets

(52) U.S. Cl.
CPC ..... *B29K 2633/12* (2013.01); *B29L 2031/752* (2013.01); *B29L 2031/753* (2013.01)

(56) References Cited

U.S. PATENT DOCUMENTS

| | | | |
|---|---|---|---|
| 2009/0012452 A1* | 1/2009 | Slepicka | A61M 1/28 604/29 |
| 2010/0018317 A1* | 1/2010 | Kitani | A61M 1/3643 73/706 |
| 2012/0038368 A1* | 2/2012 | Mahalingam | A61B 5/0536 324/603 |
| 2013/0032493 A1* | 2/2013 | Karlsson | C12Q 1/001 205/782 |
| 2014/0197101 A1* | 7/2014 | Harjes | A61M 1/16 210/637 |

FOREIGN PATENT DOCUMENTS

| | | |
|---|---|---|
| EP | 0054915 A1 | 6/1982 |
| JP | 2009-85851 | 4/2009 |
| RU | 2247365 C1 | 2/2005 |

OTHER PUBLICATIONS

Mohd Fua'ad Rahmat et al: "Electrodynamics Sensor for the Image Reconstruction Process in an Electrical Charge Tomography System," *Sensors*, vol. 9, No. 12, pp. 10291-10308, XO055119105 (Dec. 19, 2009).

Moron Z et al: "Possibilities of emplyoying a calculable four-electrode conductance cell to substitute the secondary standards of electrolytic conductivity" *Instrumentation and Measurement Technology Conference*, 1996. IMT-96 Conference Proceedings Belgium XP010163858 (Jun. 4, 1996).

C. Boveri et al., "Development of a Flow-Through Cell for Accurate Measurements of Low Electrolytic Conductivity," *XIX IMEKO World Congress Fundamental and Applied Metrology*, pp. 2619-2623 (Lisbon, Portugal Sep. 11, 2009).

J. Heller et al., "Auto-Tuned Induction Coil Conductivity sensor for In-Vivo Human Tissue Measurements," *Measurement Science Review*, vol. 9, No. 6, pp. 162-168, (2009).

Zbigniew Moron et al., "Experimental Investigations of Van Der Pauw Method Applied for Measuring Electrical Conductivity of Liquids," *XIX IMEKO World Congress Fundamental and Applied Metrology*, (Lisbon, Portugal Sep. 11, 2009).

Zbigniew Moron et al., "The Possibility of Employing a Calculable Four-Electrode Conductivity Cell to Substitute for the Secondary Standards of Electrolytic Conductivity," *IEEE Transactions on Instrumentation and Measurement*, vol. 46, No. 6, pp. 1268-1273 (Dec. 1997).

Helena M. Geirinhas Ramos et al., "Development and Characterization of a Conductivity Cell for Water Quality Monitoring," *XVIII IMEKO World Congress Metrology for a Sustainable Development*, (Rio de Janeiro, Brazil Sep. 22, 2006).

\* cited by examiner

VIEW ON ARROW 'A'

VIEW ON ARROW 'B'

LIQUID CONDUCTIVITY MEASUREMENT CELL

The present application is a 35 USC § 371 submission of international application no, PCT/GB2014/050976; filed on 27 Mar. 2014 and published in the English language on 4 Dec. 2014 with publication no, WO 2014/191715 A1, which claims the benefit of the filing date of application no. GB 1309561.7, filed 29 May 2013.

The present invention relates to a cell for the measurement of conductivity of a liquid particularly, but not exclusively, for use in preparation of dialysate solution for hemodialysis treatment.

Hemodialysis is a medical treatment which replaces, in humans, the renal function of removing excess fluid and waste products, such as potassium and urea, from blood. The treatment is either employed when renal function has deteriorated to an extent that uremic syndrome becomes a threat to the body's physiology (acute renal failure), or when a longstanding renal condition impairs the performance of the kidneys (chronic renal failure).

In hemodialysis, blood is removed from the body of a patient by an arterial line, and treated by a dialysis machine before being returned to the body by a venous line. The machine passes the blood through a dialyser containing tubes of a semi-permeable membrane. On the exterior of the semi-permeable membrane is a dialysate solution. Blood passes through the tubes, and the semi-permeable membrane filters waste products and excess fluid from the blood into the dialysate solution. The pores of the membrane allow the waste and a controlled volume of fluid to permeate into the dialysate solution whilst preventing the loss of larger more desirable molecules, like blood cells and certain proteins and polypeptides.

The action of dialysis across the membrane is achieved primarily by diffusion (the migration of molecules by random motion from a region of higher concentration to a region of lower concentration).

Fluid removal (also known in this technique as ultrafiltration) is achieved by altering the hydrostatic pressure in the dialyser, causing fluid to move across the membrane along the pressure gradient.

The dialysate solution comprises a sterilized solution of mineral ions. These ions are contained within an acid buffer and a bicarbonate buffer which are combined with sterilised water prior to delivery to the dialyser. The required composition of dialysate solution differs between patients hence it is of critical importance that dosing of the acid buffer and a bicarbonate buffer is accurate to within clinical tolerances.

The concentration of each of the acid buffer and bicarbonate base is controlled to ensure the composition of the dialysate solution is optimised for a patient.

The composition of dialysate solution can be determined to a high degree of accuracy by measuring the conductivity of the dialysate solution. Conductivity is determined by measuring the electrical current, and is variable dependent on the concentration of ions of sodium chloride in the dialysate solution.

For such measurement conventional hemodialysis machines utilise a flow through chamber having four pins arranged in a line. The chamber receives dialysate solution through an inlet and dialysate solution exits the chamber via an outlet. Other than the inlet of the chamber and the outlet of the chamber, the chamber is sealed to define a cell.

Each pin comprises an electrode. The electrodes of two of the pins generate, in use, an electric field and the electrodes of the remaining two pins are used to measure the current flowing in the generated electric field. Conventionally, the pins are located within the chamber to directly measure the conductivity of liquid passing through the cell.

In order for accurate conductivity measurements to be taken, the cross-sectional area of the chamber and the distance between the sensing pins needs to be known. Prior art flow through chambers are typically rectangular in cross-section. Therefore, an operator needs to know the width and height of the cross-section of the chamber and the distance between each of the pins in order to calibrate the cell. As a minimum, if the distances between adjacent pins are equal, the operator needs to know three variables.

A document entitled "Development of a flow-through cell for accurate conductivity measurements of low electrolytic conductivity" by C. Boveri, F. Durbiano and D. Serazio, published 2009, describes the development of a flow through cell which uses two electrodes for measuring variations in conductivity observed in water.

A document entitled "Development and characterization of a conductivity cell for water quality monitoring" by Helen M Geirinhas Ramos, A. Lopws Ribeiro. Milan Komarek and Martin Novotny, published 2006, describes the use of a four electrode flow through cell with the electrodes arranged linearly.

Each of the above referenced documents describes a flow through cell for measuring electrical conductivity of a sample material.

In some methods of use of such a cell, it is critical that the conductivity measurement is accurately measured. For example, in hemodialysis treatment, the conductivity of a dialysate solution is constantly measured to ensure that the conductivity of the dialysate solution falls within parameters specified for a particular patient. The ratio of the constituent parts of the dialysate solution, i.e. acid buffer and bicarbonate buffer, are adjusted in response to a deviation in the conductivity measurement of the dialysate solution.

It is therefore important to provide means of verifying the conductivity measurements taken by the electrodes to quickly identify if an error has occurred. In hemodialysis treatment, if the dialysate solution is of the wrong composition for a patient, the patients blood, when re-entering the patients body, may have severe health implications such as hyponatremia, hypernatremia, acidosis or alkalosis.

The present invention seeks to provide an improved liquid conductivity measurement cell.

An aspect of the invention provides a liquid conductivity measurement cell comprising a closed chamber having an inlet, an outlet and four sensing pins of substantially equal length, said sensing pins being arranged in the chamber in an orbit, each sensing pin defining an electrode, each of said electrodes being switchable between two or more electrical circuit configurations of two pins.

By the terms "arranged . . . in an orbit" and "orbital", we mean that the pins are arranged substantially equally angularly spaced around and substantially equidistant from a notional centre point.

Advantageously, arranging the four sensing pins in an orbital arrangement results in the length of said sensing pins being the only variable that an operator needs to know to calibrate the cell. The length of each sensing pin is defined as substantially the same length as any other sensing pin, the only variation being manufacturing and assembly tolerances which are readily controllable.

The orbital arrangement of sensing pins allows measurement of the conductivity of a liquid using four points of contact which take advantage of the geometry of the cell in order to remove variables in calibration of the cell. Such variables are the distance between the pins, and the cross-section of the cell, in the case of a linear arrangement of sensing pins. This is possible as the orbital arrangement of sensing pins in the cell dictates that the sensing pins are equiangularly spaced.

Two adjacent pins, in use, generate an electric field and the remaining two adjacent pins, in use, measure the conductivity of the liquid flowing through the cell. The symmetrical geometry of the cell allows for the function of the sensing pins to be switched, in use, so that the pins which are initially generating an electric field measure conductivity and vice versa.

Calibration of the cell is quicker and easier having just one the one variable instead of the plurality of variables of the prior art. The cell is calibrated on start up of a hemodialysis machine by using a pair of opposing pins to generate an electric field and the remaining pair of opposing pins to measure any current within the cell. During calibration no liquid will flow through the cell hence the current should be measured as zero. If a current is detected the hemodialysis machine recognises that the cell is not calibrated correctly.

Each sensing pin being switchable between two or more configurations allows the same set of sensing pins to be used for measuring the conductivity of a liquid flowing through the cell and verifying that the conductivity measurements taken are accurate. In one embodiment, a first configuration is a control circuit for measuring the conductivity of a liquid passing through the chamber and a second configuration is a redundancy circuit for checking the accuracy of conductivity measurements taken by the control circuit.

This arrangement is useful to indirectly and continuously monitor the composition of the dialysate solution. The provision of two circuits performing substantially the same function is necessary to detect errors in measurement of conductivity by the control circuit.

In one embodiment, the cell is a flow through cell. Measurement of the conductivity of dialysate solution is a constant process that is maintained throughout a dialysis treatment session. Use of a flow through cell ensures that a representative sample of the dialysate solution is tested at any given time. The flow through cell, having an inlet and an outlet to the chamber, also promotes mixing of the dialysate solution as the dialysate solution passes therethrough.

In one embodiment, the sensing pins are inside the chamber.

In another embodiment, the sensing pins are outside of the chamber.

In one embodiment, the inlet and outlet of the chamber are oblique. Preferably, the inlet and outlet of the chamber are unobstructed. Such a configuration promotes a swirling of the dialysate solution in the chamber to provide a mixing effect.

In another embodiment, the inlet and outlet of the chamber are radial and each obstructed by a sensing pin. Such a configuration promotes disturbance of the dialysate solution upon entry to and exit from the chamber to provide a mixing effect. In one embodiment, the sensing pins are separated from a flow through space defined in the chamber. Preferably, the chamber is defined by a plastic moulding and the sensing pins are provided outside the chamber, and preferably on a separate moulding to the chamber. The sensing pins can generate an electric field in the dialysate solution without being immersed. The sensing pins can also measure current in the generated electric field without being immersed. The sensing pins each have means of providing a signal to generate the electric field or measure current of the dialysate solution. Mounting the sensing pins external to the chamber removes the need to seal an interface where the sensing pins penetrate or are mounted to the chamber.

In one embodiment the chamber is constructed from Polymethyl Methacrylate (PMMA). Preferably the chamber comprises a base wall and a perimeter side wall extending upwardly therefrom, the chamber being closable by a diaphragm.

The chamber may be circular, square shaped or diamond shaped in cross-section. Such regular shapes facilitate the sensing pins being equi-spaced around the perimeter of the chamber. Most preferably, the chamber is circular in cross-section.

In one embodiment, the chamber is cylindrical or cuboid having a maximum width between 20 mm and 30 mm. Preferably, the width of the chamber is greater than the height of the chamber.

In one embodiment, the pins are constructed from stainless steel and are between 1 and 2 mm in diameter. In an embodiment where the pins are, in use, disposed within the chamber, the pins are preferably 25 mm to 35 mm in length. In an embodiment where the pins, in use, are disposed outside of the chamber, the pins are preferably 5 mm to 10 mm in length.

In an embodiment where the pins are disposed in the chamber they are orientated in the same direction. In one embodiment, the pins are orthogonal to the base wall of the chamber and have an electrical connection outside of the chamber.

Preferably, the pins are arranged close to the perimeter of the wall of the chamber. In one embodiment, the pins are arranged around the perimeter of the wall of the chamber and are in contact therewith. Preferably, each sensing pin comprises an electrode. In one embodiment the electrode of each pin is the portion of the pin inside the cell.

In another embodiment, the electrode of each pin is the portion of the pin outside the cell or the whole pin if the pin is completely outside of the cell.

In one embodiment, a central barrier is provided within the chamber, the barrier providing a partial restriction between the inlet and the outlet of the chamber. Preferably, the central barrier is an upstanding wall extending from the base wall of the chamber and is disposed substantially equally between the inlet and the outlet of the chamber. The central barrier is preferably an unapertured wall extending upwardly from the base wall a distance less than half the height of the cell.

Provision of a central barrier disturbs flow of a liquid as it passes through the cell. This advantageous to promote a mixing effect within the liquid as it passes through the cell.

In one embodiment, the cell is provided on a cartridge insertable into a hemodialysis machine. Preferably, the cartridge is disposable. Provision of the cell on a disposable cartridge removes the requirement to sanitize the cell after each use of the hemodialysis machine.

A further aspect of the invention provides a method of manufacturing a liquid conductivity measurement cell, the method comprising providing a channel having a base wall and two side walls extending upwardly therefrom and defining a flow path for a liquid, the channel having an aperture in the base wall; moulding a liquid conductivity measurement cell, the cell comprising a structure having a base wall and a continuous perimeter side wall extending upwardly therefrom and a plurality of sensing pins arranged within the perimeter of said side wall, the structure being shaped to substantially close the aperture in the base wall of the channel; positioning the cell such that the base wall of the structure of the cell at least substantially closes the aperture in the base wall of the channel; and, bonding the cell to the base wall of the channel.

The method of manufacture described allows for the flow path and the cell to be manufactured separately before being bonded together at a later stage. This is advantageous as manufacture of the components individually is less complex and less expensive.

In one embodiment, the method of manufacture further comprises closing the flow path with a diaphragm bonded to the side walls of the channel and closing the cell with a diaphragm bonded to the side wall of the cell.

Yet a further aspect of the invention provides a liquid conductivity measurement cell comprising a closed structure, the structure having a base wall and a continuous perimeter side wall extending upwardly therefrom, a plurality of sensing pins arranged within the perimeter of said side wall and extending a distance less than the height of the said side wall, and a diaphragm attached to the free end of the side wall, the diaphragm closing the cell.

An embodiment of the invention will now be described, by way of example only, with reference to the following figures.

Figure 1:
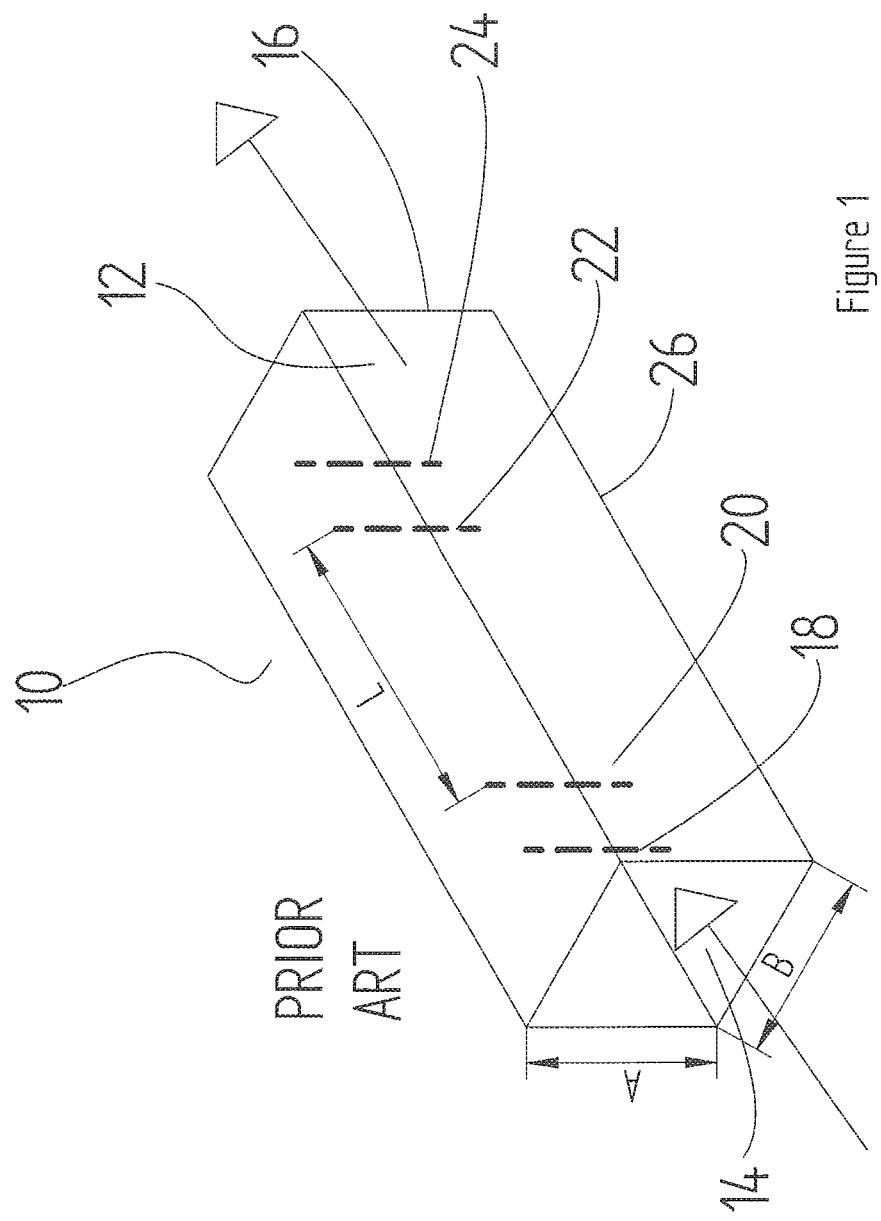
FIG. 1 shows a schematic view of a conventional prior art arrangement of flow through liquid conductivity measurement cell.

With reference to FIG. 1, a conventional prior art liquid conductivity measurement cell is shown. The cell 10 comprises a chamber 12 having an inlet 14 and an outlet 16. Four sensing pins 18, 20, 22, 24 are spaced apart in a line within the chamber 12. Each sensing pin is arranged to be orthogonal to the base 26 of the cell. The chamber 12 of the cell 10 has a continuous cross-section having a height A and a width B. Each sensing pin 18, 20, 22, 24 is substantially the same length within the chamber 12 of the cell 10.

The outermost sensing pins 18, 24 are used to generate an electric field and the innermost sensing pins 20, 22 are used to measure conductivity of a liquid, i.e. dialysate solution, flowing through the electric field.

Prior to use, the cell 10 requires calibrating in a known manner to ensure that the conductivity measurement taken by the sensing pins 20, 22 is accurate. In order to calibrate the cell 10, a cell constant ($K_{CELL}$) needs to be determined. In the case of a rectangular flow through cell, the cell constant is determined by:

$$K_{CELL} = \frac{\text{Distance between innermost sensing pins } (L)}{\text{Cross section of cell } (A \times B)} \quad (1.1)$$

Calibration of the prior art flow through cell 10 shown in FIG. 1 requires three variables to be known:
1) The distance between the innermost sensing pins (L)
2) The height of the cell (A)
3) The width of the cell (B)

Figure 2:
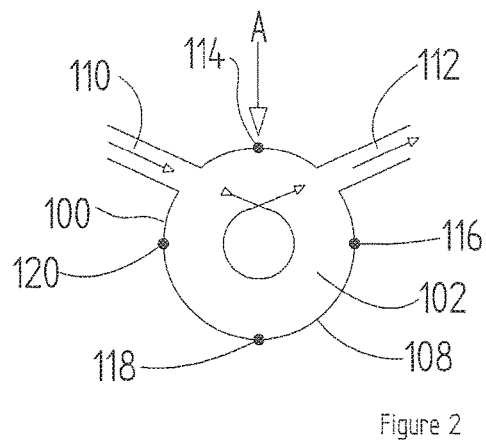
FIG. 2 shows a plan view of a schematic arrangement of a flow through liquid conductivity measurement cell according to a first embodiment of a first aspect of the invention.
Figure 3:
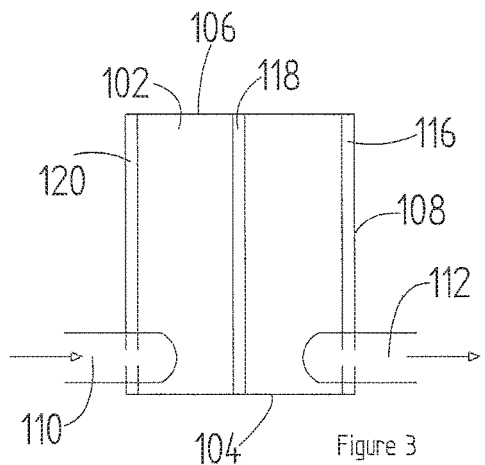
FIG. 3 shows a view on Arrow A of the schematic arrangement of FIG. 2.

Referring to FIGS. 2 and 3, a flow through cell 100 according to the invention comprises a closed chamber 102 having a base wall 104, a top wall 106, a continuous perimeter side wall 108, an inlet 110 and an outlet 112. The chamber 102 of the cell 100 is cylindrical and is provided with four sensing pins 114, 116, 118, 120 equiangularly spaced within the perimeter side wall 108 of the chamber 102. The chamber 102 is constructed from a medical grade plastic material such as Polymethyl Methacrylate (PMMA) and has a maximum width of 20 mm.

In the illustrated embodiment, the sensing pins 114, 116, 118, 120 are shown adjacent to the perimeter sidewall 108 of the chamber 102. It is also possible for the sensing pins 114, 116, 118 and 120 to be spaced away equally from the perimeter side wall 108 of the chamber.

The inlet 110 and the outlet 112 of the chamber 102 are arranged tangentially to the chamber 102, and unobstructed. The inlet 110 of the chamber 102 is positioned between two sensing pins 114, 120 and the outlet 106 of the chamber 102 is also positioned between two sensing pins 114, 116. Each sensing pin. 114, 116, 118, 120 extends upwardly into the chamber 102 by a distance h from the base wall 104 of the chamber 102 and is arranged orthogonal thereto. Each sensing pin 114, 116, 118, 120 has a substantially equal length of up to 35 mm, with up to 25 mm of the length of each pin 114, 116, 118, 120 being positioned within the cell 100, and a cross-sectional area between 1 and 4 mm². The sensing pins 114, 116, 118, 120 are made of stainless steel.

The position of each of the sensing pins 114, 116, 118, 120 is fixed around an orbit within the chamber 102 with each of the sensing pins 114, 116, 118, 120 being equiangularly spaced apart. Each sensing pin 114, 116, 118, 120 has an electrode capable of generating an electrical field and measuring the conductivity of a liquid flowing through the cell 100. The electrode of each sensing pin 114, 116, 118, 120 is the same as the electrode of any other sensing pin 114, 116, 118, 120 within the chamber 102 and is disposed toward the free end of each of said sensing pins 114, 116, 118, 120.

An electrical wire within each sensing pin connects the respective electrodes to at least two independent electrical circuits, each electrical circuit performing a function independent to that of any other electrical circuit. In a preferred embodiment, a first electrical circuit is defined as a control circuit and a second electrical circuit is defined as a redundancy circuit. The function of each electrical circuit will be described later.

Prior to use, the cell 100 requires calibrating based on a cell constant $K_{CELL}$ which is determined from:

$$K_{CELL} = \frac{\ln 2}{\Pi h} \quad (1.2)$$

During calibration of the cell 100, opposing pins 114, 118, for example, selected to generate an electric field and opposing pins 116, 120 are selected to measure the current within the electric field. Selection of opposing sensing pins 114, 118 or 116, 120 generates a symmetric electric field which should result in a zero conductivity measurement being detected by the other opposing sensing pins. If a non-zero measurement is detected, a correction factor is applied or a solution of known conductivity is flowed through the cell. Either approach should result in a zero conductivity measurement being detected. Calibration of the cell is conducted periodically to detect for variations in the conductivity value being detected. If there is a variance over time, both the control circuit and the redundancy circuit are known to be at fault.

In use, dialysate solution enters the chamber 102 through the inlet 110 of the chamber 102 and swirls therein before exiting the chamber 102 through the outlet 112 of the chamber 102. Swirling of the dialysate solution within the chamber 102 is caused by the tangential arrangement of the inlet 110 and the outlet 112 of the chamber 102.

As the dialysate solution flows through the chamber 102, two adjacent sensing pins, i.e. sensing pins 114, 120, are used to generate an electrical field within the chamber 102 and the other two adjacent sensing pins, i.e. sensing pins 116, 118, are used to measure the conductivity of the dialysate solution passing through the electrical field. The operation of the sensing pins switches at pre-determined intervals so that sensing pins 114, 120, which are initially used to generate an electric field within the chamber, would measure conductivity and sensing pins 116, 118, which are initially used to measure conductivity, would generate an electric field.

The control circuit, in use, measures conductivity of a liquid, i.e. dialysate solution, passing through the cell 100 and controls a hemodialysis machine accordingly, i.e. by introducing dialysate solution constituents, i.e. bicarbonate buffer and acid buffer, into the dialysate solution to adjust the conductivity thereof in a known manner. The redundancy circuit checks the measurements taken by the control circuit to determine whether the control circuit is functioning correctly and should give the same readings. If an error is detected, the hemodialysis machine stops the dialysis process.

Each electrode switches between circuits at pre-determined time intervals so that the sensing pins 108, 110, 112, 114 are connected to the control circuit for a first time period and to the redundancy circuit for a second time period. The circuits switch operation automatically after a pre-determined time interval. However, in some embodiments, operation of the circuits could be switched manually.

Figure 4:
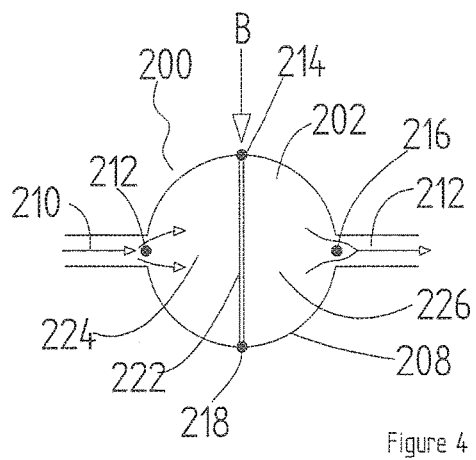
FIG. 4 shows a plan view of a schematic arrangement of a flow through liquid conductivity measurement cell according to a second embodiment of the first aspect of the invention.
Figure 5:
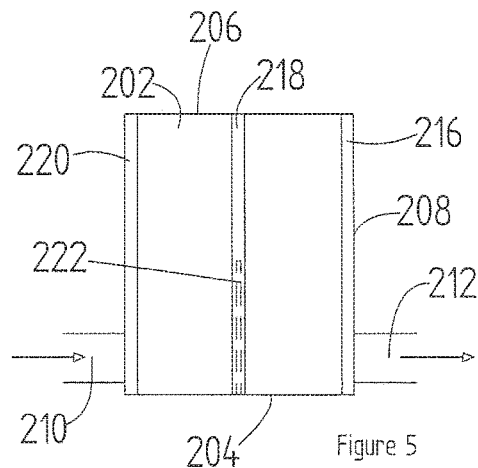
FIG. 5 shows a view on Arrow B of the schematic arrangement of FIG. 4.

Referring to FIGS. 4 and 5, a second embodiment of flow through cell is shown. Unless otherwise specified, the flow through cell 200 illustrated in FIGS. 4 and 5 is equivalent to the flow through cell 100 illustrated in FIGS. 2 and 3.

The flow through cell 200 comprises a closed chamber 202 having a base wall 204, a top wall 206, a continuous perimeter side wall 208, an inlet 210 and an outlet 212. The chamber 202 of the cell 200 is cylindrical and is provided with four sensing pins 214, 216, 218, 220 equiangularly spaced within the perimeter side wall 208 of the chamber 202. The chamber 202 is constructed from a medical grade plastic material such as Polymethyl Methacrylate (PMMA). Unless otherwise specified, the flow through cell 200 illustrated in FIGS. 4 and 5 is equivalent to the flow through cell 100 illustrated in FIGS. 2 and 3.

The inlet 210 and the outlet 212 of the chamber 202 are arranged radially to the chamber 202, and each may be obstructed by a sensing pin 216, 220 to disturb flow of dialysate solution entering and exiting the chamber 202. The inlet 210 of the chamber 202 is positioned in-line with a sensing pin 220 and the outlet 206 of the chamber 202 is also positioned in-line with a sensing pin 216. Each sensing pin, 214, 216, 218, 220 extends upwardly into the chamber 202 by a distance h from the base wall 204 of the chamber 202 and is arranged orthogonal thereto.

A dividing barrier 222, in the form of an upstanding wall, is provided within the chamber 202 to further disturb flow of dialysate solution through the chamber 202. The upstanding wall 222 is unapertured and has a height less than half of that of the cell 200. The wall 222 is positioned approximately centrally within the chamber 202 such that a first part 224 of the chamber 202 has a volume substantially equal to a second part 226 of the chamber 202.

Dialysate solution enters the chamber 202 through the inlet 210 of the chamber 202 and fills a first part 224 of the chamber 202 adjacent to the inlet 210 of the chamber 202. When the level of dialysate solution within the first part 224 of the chamber 202 reaches a level higher than the barrier 214, the dialysate solution enters a second part 218 of the chamber 220 adjacent to the outlet 204 of the chamber 220 and exits the chamber 220 through the outlet 204 of the chamber 220.

Figure 6:
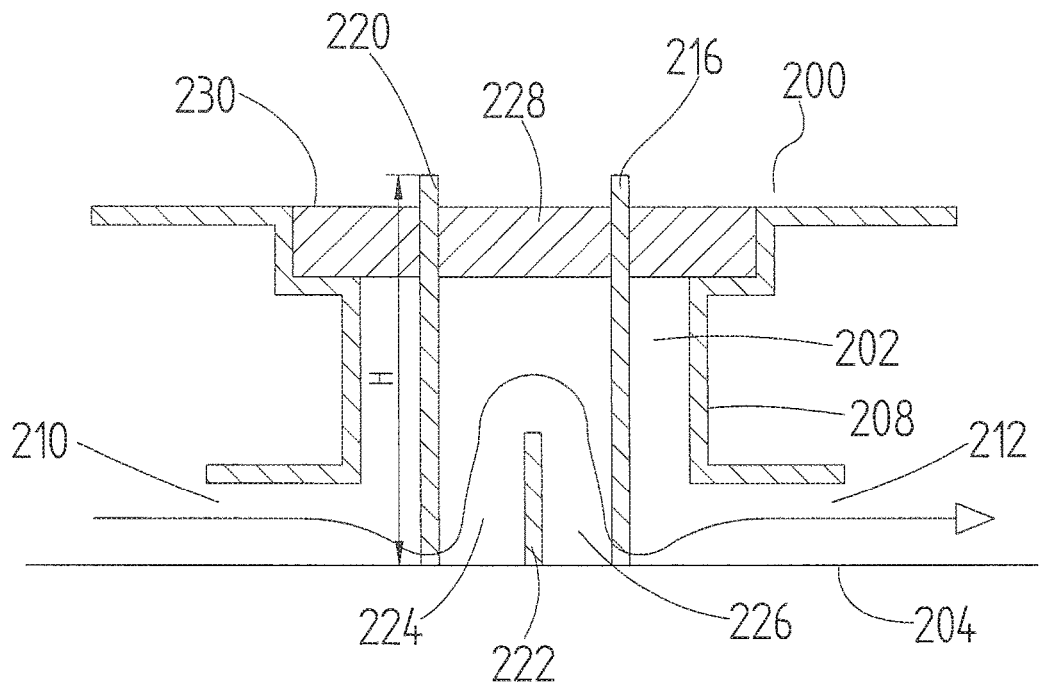
FIG. 6 shows a schematic arrangement of a fluid path through a flow through liquid conductivity measurement cell according to a third embodiment of the first aspect of the invention.

Referring to FIG. 6, a variation of the liquid conductivity measurement cell of FIG. 5 is shown. The sensing pins 214, 216, 218, 220 are shown as an integral part of an insert moulding 228 closing an opening to the chamber 202. The insert moulding 228 is ultrasonically welded to the chamber 202 with the pins 214, 216, 218, 220 extending through the insert moulding 228 into the chamber 202. Each sensing pin 214, 216, 218, 220 abuts against the base wall 204 of the chamber 202 to control the length of the sensing pins 214, 216, 218, 220 inside the chamber 202 of the cell. In some embodiments the sensing pins 214, 216, 218, 220 may be shorter and define a gap between the free end of each sensing pin 214, 216, 218, 220 and the base wall 204 of the chamber 202. The insert moulding 228 is constructed from a medical grade plastic material such as Polymethyl Methacrylate.

Figure 7:
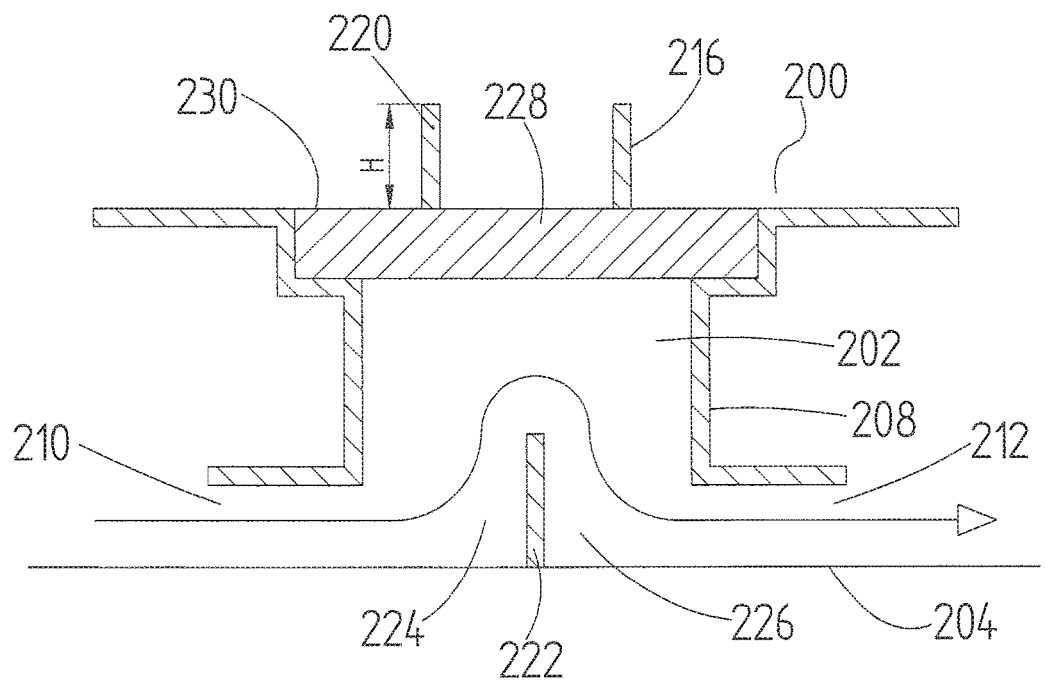
FIG. 7 shows a schematic arrangement of a fluid path through a flow through liquid conductivity measurement cell according to a fourth embodiment of the first aspect of the invention.

Referring to FIG. 7, another variation of the liquid conductivity measurement cell of FIG. 5 is shown. Each sensing pin 214, 216, 218, 220 is attached to an outer face 230 of the insert moulding 228 and hence does not penetrate into the chamber 202 at all. The sensing pins in this embodiment each have a nominal length of 6 mm. The electrical field is generated through the insert moulding 228 and the current of the liquid flowing through the chamber 202 of the cell 200 is sensed through the insert moulding 228.

Figure 8A:
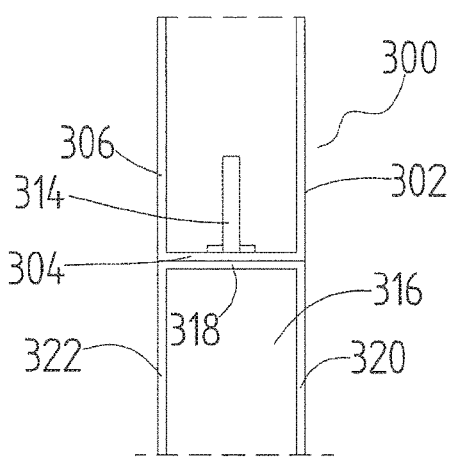
FIGS. 8a and 8b show schematic arrangements of an enclosed liquid conductivity measurement cell according to an embodiment of a second aspect of the invention.
Figure 8B:
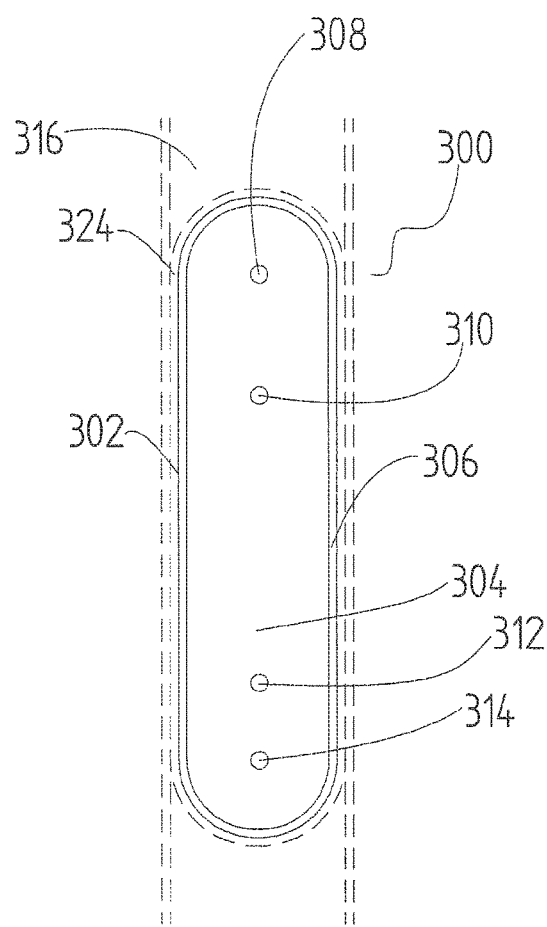

Referring to FIGS. 8a and 8b, an alternative liquid conductivity measurement cell 300 is shown. The cell 300 comprises an elongate, oblong shaped body 302 having a base wall 304 and a perimeter side wall 306 extending upwardly therefrom. Four sensing pins 308, 310, 312, 314, arranged in a line, are moulded into the base wall 304 and extend upwardly therefrom. The sensing pins 308, 310, 312, 314 are nominally 6 mm in length and between 1 and 4 mm$^2$ in cross-sectional area.

The cell 300 is moulded from a medical grade plastic material such as Polymethyl Methacrylate (PMMA) and, in use, is bonded to a channel 316 which defines a liquid flow path. The channel 316 comprises a base wall 318 and two opposing side walls 320, 322 extending upwardly therefrom. The channel 316 is provided with an aperture 324 in the base wall 318 corresponding substantially to the dimensions of the cell 300. When positioned in the aperture 324, the cell 300 substantially closes the aperture 324 and is bonded to the base wall 318 of the channel 316 by, for example, ultrasonic welding. The channel 316 is closed by diaphragm (not shown) which is bonded to the ends of the side walls 320, 322 of the channel. The cell 300 is closed by a diaphragm (not shown) which is bonded to the end of the perimeter side wall 306 of the cell 300.

The channel 316 described above is typically part of a disposable cartridge used in hemodialysis machine.

In use, the outermost sensing pins 308, 314 generate an electrical field and the innermost sensing pins 310, 312 measure the conductivity of dialysate solution flowing through the channel.

A method of manufacturing the cell 300 comprises:

(a) providing a flow path for a liquid, the flow path being defined by a channel 316 having a base wall 318, two sides walls 320, 322 extending perpendicularly therefrom, the channel 316 further having an aperture 324 in the base wall 318;

(b) moulding a liquid conductivity measurement cell 300, the cell 300 comprising a structure having a base wall 304 and a perimeter side wall 302 extending perpendicularly therefrom, the structure being sized to substantially correspond with the aperture 324 in the base wall 318 of the channel;

(c) positioning the cell 300 such that the base wall 304 of the structure of the cell 300 at least substantially closes the aperture 324 in the base wall 318 of the channel 316; and, (d) bonding the cell 300 to the base wall 318 of the channel 300.

It will be appreciated that the method of manufacturing the cell 300 could, with minor modifications be applied to cells 100, 200. For example, cells 100, 200 would extend through the aperture 324 in the base wall 318 of the channel 316, defining the liquid flow path, to permit dialysate solution to flow from the channel 316 and through the cell 100, 200.

The embodiments of the present invention, described with reference to FIGS. 2 to 8a and 8b, are examples only and do not exclude variations therefrom from the scope of the invention as defined by the claims.

The invention claimed is:

1. A liquid conductivity measurement flow through cell comprising:
 a chamber having a longitudinal axis, and having an inlet and an outlet, a longitudinal axis of the inlet being substantially perpendicular to a first plane that includes the longitudinal axis of the chamber, and a longitudinal axis of the outlet being substantially perpendicular to a second plane, the second plane being selected from a group consisting of the first plane and any other plane that includes the longitudinal axis of the chamber;
 four sensing pins, said sensing pins being arranged in an orbit around the longitudinal axis of the chamber, each of the sensing pins being substantially parallel to the longitudinal axis of the chamber;
 each of the four sensing pins defining an electrode;
 each of said electrodes being switchable between two or more configurations of two of the four sensing pins.

2. The liquid conductivity measurement cell according to claim 1, wherein a first configuration of the two or more configurations defines a control circuit for measuring conductivity of a liquid passing through the chamber, and a second configuration of the two or more configurations defines a redundancy circuit for checking accuracy of conductivity measurements taken by the control circuit.

3. The liquid conductivity measurement cell according to claim 1, wherein each of the four sensing pins is separated from a flow through space defined in the chamber.

4. The liquid conductivity measurement cell according to claim 1, wherein each of the four sensing pins extends into the chamber.

5. The liquid conductivity measurement cell according to claim 1, wherein the chamber is defined by a plastic moulding.

6. The liquid conductivity measurement cell according to claim 5, wherein each of the four sensing pins is provided on a common plastic moulding independent of the plastic moulding defining the chamber.

7. The liquid conductivity measurement cell according to claim 6, wherein the moulding for the sensing pins is bonded to the chamber by ultrasonic, thermal or adhesive bonding.

8. The liquid conductivity measurement cell according to claim 1, wherein each of the four sensing pins has a substantially similar cross-sectional area.

9. The liquid conductivity measurement cell according to claim 1, wherein each of the four sensing pins has a substantially similar length.

10. The liquid conductivity measurement cell according to claim 1, wherein the longitudinal axis of the inlet forms an oblique angle with a radius of the chamber, and the longitudinal axis of the outlet forms an oblique angle with a radius of the chamber.

11. The liquid conductivity measurement cell according to claim 10, wherein the inlet of the chamber is disposed between two of the four sensing pins and the outlet of the chamber is disposed between two of the four sensing pins.

12. The liquid conductivity measurement cell according to claim 11, wherein, in use, the inlet of the chamber is disposed between two of the four sensing pins, each one of the two sensing pins, between which the inlet is disposed, being configured to measure a current in a liquid flowing through the cell in a first configuration of the two or more configurations.

13. The liquid conductivity measurement cell according to claim 12, wherein, in use, the outlet of the chamber is disposed between two of the four sensing pins, one of the two sensing pins, between which the outlet is disposed, being configured to measure a current in the liquid flowing through the cell and one of the two sensing pins, between which the outlet is disposed, being configured to generate an electrical field within the chamber, in the first configuration.

14. The liquid conductivity measurement cell according to claim 10, wherein the inlet and the outlet of the chamber are unobstructed.

15. The liquid conductivity measurement cell according to claim 1, wherein the longitudinal axis of the inlet and the longitudinal axis of the outlet of the chamber substantially coincide with each other.

16. The liquid conductivity measurement cell according to claim 15, wherein the inlet and the outlet of the chamber are obstructed.

17. The liquid conductivity measurement cell according to claim 16, wherein one of the four sensing pins obstructs the inlet of the chamber.

18. The liquid conductivity measurement cell according to claim 17, wherein one of the four sensing pins obstructs the outlet of the chamber.

19. The liquid conductivity measurement cell according to claim 1, wherein the chamber is circular in cross-section.

20. The liquid conductivity measurement cell according to claim 1, wherein the chamber is square in cross-section.

21. The liquid conductivity measurement cell according to claim 1, wherein the chamber is diamond in cross-section.

22. The liquid conductivity measurement cell according to claim 19, wherein the chamber has a constant cross-section.

23. The liquid conductivity measurement cell according to claim 19, wherein each of the four sensing pins is arranged adjacent to a perimeter of the chamber.

24. The liquid conductivity measurement cell according to claim 16, wherein a central barrier is provided within the chamber, the barrier providing a partial restriction to flow between the inlet and the outlet of the chamber.

25. The liquid conductivity measurement cell according to claim 24, wherein the chamber comprises a base wall and a continuous perimeter side wall extending upwardly therefrom.

26. The liquid conductivity measurement cell according to claim 25, wherein the central barrier comprises an un-apertured wall extending from the base wall of the chamber.

27. The liquid conductivity measurement cell according to claim 2, wherein each of the electrodes automatically alternates between being connected to the control circuit and the redundancy circuit.

28. The liquid conductivity measurement cell according to claim 27, wherein alternation between the circuits automatically occurs at a pre-determined time interval.

29. The liquid conductivity measurement cell according to claim 1, wherein a cross-sectional area of each sensing pin is less than five square millimeters.

30. The liquid conductivity measurement cell according to claim 1, wherein a length of each of the four sensing pins is between 6 mm and 35 mm.

31. The liquid conductivity measurement cell according to claim 1, wherein a maximum width of the cell is less than 25 mm.

32. The liquid conductivity measurement cell according to claim 1, wherein the cell is provided on a cartridge insertable into a hemodialysis machine.

33. The liquid conductivity measurement cell according to claim 32, wherein the cartridge is disposable.

* * * * *